US012624093B2

(12) United States Patent
McBride et al.

(10) Patent No.: US 12,624,093 B2
(45) Date of Patent: May 12, 2026

(54) *EHRLICHIA* VACCINES AND IMMUNOGENIC COMPOSITIONS

(71) Applicants:Research Development Foundation, Carson City, NV (US); Zoetis Services LLC, Parsippany, NJ (US)

(72) Inventors: Jere W. McBride, Galveston, TX (US); Paul J. Dominowski, Kalamazoo, MI (US); Suman Mahan, Kalamazoo, MI (US); Jason J. Millership, Kalamazoo, MI (US); Duncan M. Mwangi, Kalamazoo, MI (US); Sharath Rai, Kalamazoo, MI (US); Sharon M. Wappel, Kalamazoo, MI (US)

(73) Assignees: Research Development Foundation, Carson City, NV (US); Zoetis Services LLC, Parsippany, NJ (US)

( * ) Notice: Subject to any disclaimer, the term of this patent is extended or adjusted under 35 U.S.C. 154(b) by 1102 days.

(21) Appl. No.: 17/626,866

(22) PCT Filed: Jul. 13, 2020

(86) PCT No.: PCT/US2020/041779
§ 371 (c)(1),
(2) Date: Jan. 13, 2022

(87) PCT Pub. No.: WO2021/011456
PCT Pub. Date: Jan. 21, 2021

(65) Prior Publication Data
US 2022/0356231 A1     Nov. 10, 2022

Related U.S. Application Data

(60) Provisional application No. 63/049,476, filed on Jul. 8, 2020, provisional application No. 62/879,762, filed on Jul. 29, 2019, provisional application No. 62/873,843, filed on Jul. 12, 2019.

(51) Int. Cl.
| | |
|---|---|
| *A61K 39/00* | (2006.01) |
| *A61K 39/02* | (2006.01) |
| *A61K 39/39* | (2006.01) |
| *C07K 14/29* | (2006.01) |
| *C07K 16/12* | (2006.01) |
| *C07K 16/1246* | (2026.01) |

(52) U.S. Cl.
CPC ...... *C07K 16/1246* (2013.01); *A61K 39/0233* (2013.01); *A61K 39/39* (2013.01); *C07K 14/29* (2013.01); *A61K 2039/521* (2013.01); *A61K 2039/552* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 7,204,992 | B2 | 4/2007 | McBride et al. |
| 7,722,880 | B2 | 5/2010 | McBride et al. |
| 8,329,189 | B2 | 12/2012 | McBride et al. |
| 8,580,280 | B2 | 11/2013 | Dominowski et al. |
| 8,980,288 | B2 | 3/2015 | Diehl et al. |
| 9,250,240 | B2 | 2/2016 | McBride et al. |
| 9,545,439 | B2 | 1/2017 | Diehl et al. |
| 9,645,148 | B2 | 5/2017 | McBride et al. |
| 9,662,385 | B2 | 5/2017 | Dominowski et al. |
| 9,814,768 | B2 | 11/2017 | McBride et al. |
| 10,117,921 | B2 | 11/2018 | Dominowski et al. |
| 10,131,705 | B2 | 11/2018 | McBride et al. |
| 10,238,736 | B2 | 3/2019 | Dominowski et al. |
| 11,459,379 | B2 | 10/2022 | McBride et al. |
| 11,780,892 | B2 | 10/2023 | McBride et al. |
| 2009/0005535 | A1 | 1/2009 | Kadzimirzs et al. |
| 2019/0008953 | A1 | 1/2019 | Dominowski et al. |
| 2019/0038737 | A1 | 2/2019 | Dominowski et al. |
| 2021/0239695 | A1 | 8/2021 | McBride et al. |

FOREIGN PATENT DOCUMENTS

| | | |
|---|---|---|
| CN | 109675029 A | 4/2019 |
| EP | 2433646 | 3/2012 |
| WO | WO2000/12688 | 3/2000 |
| WO | WO2004/042037 | 5/2004 |
| WO | WO2005/087803 | 9/2005 |
| WO | WO2005/097803 | 10/2005 |
| WO | WO2006/138509 | 12/2006 |
| WO | WO2008/000068 | 1/2008 |
| WO | WO2008/043000 | 4/2008 |
| WO | WO2008/112007 | 9/2008 |
| WO | WO2009/156960 | 12/2009 |
| WO | WO2010/126993 | 11/2010 |

(Continued)

OTHER PUBLICATIONS

Aguiar et al. "Detection of genotype-specific Ehrlichia canis exposure in Brazilian dogs by TRP36 peptide ELISA" *Ticks Tick Borne Dis.*, 7(1):142-145, 2016.

Bonam et al., "An Overview of Novel Adjuvants Designed for Improving Vaccine Efficacy", *Trends in Pharmacological Sciences*, 38(9): 771-778, 2017.

Cardenas et al., "Enzyme-linked immunosorbent assay with conserved immunoreactive glycoproteins gp36 and gp19 has enhanced sensitivity and provides species-specific immunodiagnosis of Ehrlichia canis infection", *Clinical and Vaccine Immunology, American Society for Microbiology*, 14(2):123-128, 2007.

Carpino et al., « Rapid, Continuous Solution-Phase Peptide Synthesis : Application to Peptides of Pharmaceutical Interest », *Org. Proc. Res. Dev.*, 7(1)28-37, 2003.

(Continued)

*Primary Examiner* — S. Devi

(74) *Attorney, Agent, or Firm* — pH IP Law

(57) ABSTRACT

Provided herein are immunogenic compositions that may be used, in some aspects, to induce an immune response against an *Ehrlichia* such as *Ehrlichia canis*. In some embodiments, the immunogenic composition comprises an *E. canis* bacterin and/or adjuvant, such as for example an emulsion or liposomal adjuvant. Related methods such as for diagnosis of or vaccination against ehrlichiosis are also provided.

7 Claims, No Drawings

Specification includes a Sequence Listing.

(56)        References Cited

FOREIGN PATENT DOCUMENTS

| | | |
|---|---|---|
| WO | WO2011/148356 | 12/2011 |
| WO | WO2013/181086 | 12/2013 |
| WO | WO2014/186291 | 12/2014 |
| WO | WO2015/042369 | 3/2015 |
| WO | WO2020/023950 | 1/2020 |

OTHER PUBLICATIONS

Doyle et al., "Differentially expressed and secreted major immunoreactive protein orthologs of ehrlichia canis and E-chaffeensis elicit early antibody responses to epitopes on glycosylated tandem repeats", *Infection and Immunity*, 74(1), 2006.

Dumler et al., « Ehrlichioses in Humans: Epidemiology, Clinical Presentation, Diagnosis, and Treatment, *Clin. Infect. Dis.*, 45:S45-S51, 2007.

Eddlestone et al., "Doxycycline Clearance of Experimentally Induced Chronic Ehrlichia canis Infection in Dogs", *Journal of Veterinary Internal Medicine*, 21(6):1237-1242, 2007.

Extended European Search Report for EP20751422.5 dated Mar. 26, 2024, 3 pages.

Fishbein et al., « Human ehrlichiosis in the United States, 1985 to 1990, *AnnInternMed* 120:736-743, 1994.

International Preliminary Search Report and Written Opinion for International Application No. PCT/US2020/041779 dated Jan. 18, 2022, 13 pages.

International Search Report and Written Opinion for International Application No. PCT/US2020/041779 dated Nov. 10, 2020, 21 pages.

Kuriakose et al., "Molecular basis of antibody mediated immunity against Ehrlichia chaffeensis involves species-specific liner epitopes in tandem repeat proteins", *Microbes and Infection*, 14(12):1054-1063, 2012.

Luo et al., "Major species-Specific antibody eoptopes of the ehrlichia chaffeensis p120 and E-canis P140 orthologs in surface-exposed tandem repeat regions", *Clincial and Vaccine Immunology*, 16(7), 2009.

Mcbride et al. "A conserved, transcriptionally active p28 multigene locus of *Ehrlichia canis*", Gene. 254(1-2):245-52, 2000.

Mcbride et al., "Tyrosine-Phosphorylated *Ehrlichia chaffeensis* and *Ehrlichia canis* Tandem Repeat Orthologs Contain a Major Continuou Cross-Reactive Antibody Epitope in Lysine-Rich Repeats", *Infect Immun.* 79(8):3178-87, 2011.

Olano et al., "Human monocytotropic ehrlichiosis, Missouri." *Emerg Infect Dis* 9:1579-1586, 2003.

Paparone et al., Ehrlichiosis with pancytopenia and ARDS. New Jersey Med 92(6):381-385, 1995.

Stuen, et al., "Lambs immunized with an inactivated variant of *Anaplasma phagocytophilum*" Acta Vet Scand, 57:40, 2015.

Tollersrud et al., "*Staphylococcus aureus* capsular polysaccharide type 5 conjugate and whole cell vaccines stimulate antibody responses in cattle." (2001) *Vaccine* 19(28-29):3896-3903.

Vega et al., *Anaplasma marginale* field challenge: Protection by an inactivated immunogen that shares partial sequence of mspla variable region with the challenge strain, Vaccine, 25, pp. 519-525, 2007.

Walker and Dumler, Human monocytic and granulocytic ehrlichioses. Discovery and diagnosis of emerging tick-borne infections and the critical role of the pathologist. *Archives of Pathology & Laboratory Medicine* 121(8):785-791, 1997.

Walker et al., "Ehrlichia chaffeensis: a prevalent, life-threatening, emerging pathogen." *Trans Am Clin Climatol Assoc* 115:375-382; discussion 382-374, 2004.

Zhu et al., "Ehrlichia chaffeensis TRP120 binds a G+C-rich motif in host cell DNA and exhibits eukaryotic transcriptional activator function", *Infect Immun.*, 79(11):4370-812011.

EHRLICHIA VACCINES AND IMMUNOGENIC COMPOSITIONS

This application is a national phase application under 35 U.S.C. § 371 of International Application No. PCT/US2020/041779, filed Jul. 13, 2020, which claims the benefit of United States Provisional Patent Application No. 62/873,843, filed Jul. 12, 2019, U.S. Provisional Patent Application No. 62/879,762, filed Jul. 29, 2019, and U.S. Provisional Patent Application No. 63/049,476, filed Jul. 8, 2020, the entirety of each of which is incorporated herein by reference.

BACKGROUND OF THE INVENTION

1. Field of the Invention

The present invention relates generally to the field of molecular biology and medicine. More particularly, it concerns immunogenic or vaccine compositions against *Ehrlichia canis* and related methods.

2. Description of Related Art

Human monocytotropic ehrlichiosis (HME) is a group 1 NIAID emerging disease, and the etiologic agent, *Ehrlichia chaffeensis*, is classified as a Category C priority pathogen. HME is an undifferentiated febrile illness that is life-threatening, clinical diagnosis is difficult, and definitive diagnosis is most often retrospective (Walker and Dumler, 1997; Walker et al., 2004; Dumler et al., 2007). Although well over 8,000 cases have been reported to the Centers for Disease Control as of 2012, this number likely underestimates the actual number of cases by 100-fold (Olano et al., 2003). The disease is often undiagnosed due to the non-specific symptoms associated with the onset, but it results in patient hospitalization in 43-62% of cases (Fishbein et al., 1994). Progression of the disease can result in a fatal outcome and often involves multisystem failure, with acute respiratory distress syndrome (ARDS) and meningoencephalitis being common in many fatal cases (Fishbein et al., 1994; Paparone et al., 1995). The threat to public health is increasing with newly emerging ehrlichial agents, yet vaccines for human ehrlichioses are not available, and therapeutic options are limited. *Ehrlichia canis* (*E. canis*) is a related organism that can infect dogs and causes similar veterinary and clinical problems. Clearly, there is a need for new and improved methods for diagnosing and vaccinating against *Ehrlichia* such as *E. canis*.

SUMMARY OF THE INVENTION

The present invention, in some aspects, overcomes limitations in the prior art by providing new compositions and methods that may be used to generate an immune response against *Ehrlichia canis*. In some embodiments, the composition contains at least two *E. canis* proteins or immunogenic peptides and an adjuvant, as described herein. Related methods for generating an immune response against *E. canis* are also provided. In some embodiments, an immune response can be induced in a mammalian subject (e.g., a dog) by administering to the subject: (i) an *E. canis* bacterin, (ii) an adjuvant (e.g., comprising Quil A, cholesterol, and an immunostimulatory oligonucleotide), and (iii) one or more TRP proteins or peptides, and these components may be administered in a single pharmaceutical composition (comprising the bacterin, the adjuvant, and the one or more TRP protein or peptides) or in multiple pharmaceutical compositions. For example, the subject may be administered both a first pharmaceutical composition (comprising the TRP protein(s) and the adjuvant), and a second pharmaceutical composition (comprising the bacterin and the adjuvant), wherein the first pharmaceutical composition and the second pharmaceutical composition are administered at substantially the same time or at different times.

In some aspects, the invention relates to an immunogenic composition comprising: (i) at least 1, 2, 3, 4, 5, 6, or all of TRP153, TRP36, TRP140, TRP28, TRP95, TRP 19, and/or TRP120 (e.g., TRP140, TRP36, and/or TRP19); and at least 1, 2, 3, 4, 5, or more peptides comprising or consisting of a peptide of any one of SEQ ID NOs:1-16; (ii) at least 2, 3, 4, 5, 6, or all of TRP153, TRP36, TRP140, TRP28, TRP95, TRP19 and/or TRP120 (e.g., TRP140, TRP36, and/or TRP19); (iii) an *E. canis* bacterin and at least 1, 2, 3, 4, 5, 6, or all of TRP153, TRP36, TRP140, TRP28, TRP95, TRP19, or TRP120 (e.g., TRP140, TRP36, and/or TRP19); (iv) an *E. canis* bacterin and at least 1, 2, 3, 4, 5, or more peptides comprising or consisting of a peptide of any one of SEQ ID NOs:1-16; or (v) an *E. canis* bacterin, at least 1, 2, 3, 4, 5, 6, or all of TRP153, TRP36, TRP140, TRP28, TRP95, TRP19, TRP120 (e.g., TRP140, TRP36, and/or TRP19) and at least 1, 2, 3, 4, 5, or more peptides comprising or consisting of a peptide of any one of SEQ ID NOs:1-16; and a pharmaceutically acceptable excipient. Optionally, the immunogenic composition may comprise 1, 2, 3, all of Ank200, Ank153, OMP-1 and/or P30/28. In some embodiments, the immunogenic composition does not include TRP120. In some embodiments, the pharmaceutically acceptable excipient comprises or consists of an adjuvant. In some embodiments, the adjuvant comprises a triterpenoid saponin (e.g., Quil A), a sterol (e.g., cholesterol), and an immunostimulatory oligonucleotide (e.g., a CpG-containing ODN). In some embodiments, the triterpenoid saponin is Quil A, the sterol is cholesterol, and the immunostimulatory oligonucleotide is a CpG-containing ODN. The CpG-containing ODN may be 5' JU*C-G*T*C*G*A*C*G*A*T*C*G*G*C*G*G*C*C*G*C* G*T 3' (SEQ ID NO:17), wherein "*" refers to a phosphorothioate bond, "-" refers to a phosphodiester bond, and "JU" refers to 5'-Iodo-2'-deoxyuridine. The composition may comprise at least one, at least two, or all of TRP140, TRP36, and/or TRP19. The composition may comprise a chimeric protein comprising 1, 2, or all of TRP140, TRP36, and/or TRP19. The composition may comprise a polypeptide comprising 1, 2, or all of SEQ ID NO:1, SEQ ID NO:3, and/or SEQ ID NO:14. The adjuvant may be an emulsion or liposomes, or the adjuvant may comprise a lipid. In some embodiments, the emulsion is an oil-in-water (O/W) emulsion or a water-in-oil (W/O) emulsion. The adjuvant may comprise a triterpenoid, a sterol, an immunomodulator, a polymer, and/or an immunostimulatory oligonucleotide. In some embodiments, the polymer is diethyl-aminoethyl (DEAE)-dextran, polyethelyne glycol, or polyacrylic acid. The immunostimulatory oligonucleotide may be a CpG containing ODN. In some embodiments, the adjuvant comprises DEAE Dextran, an immunostimulatory oligonucleotide, and oil such as mineral oil, wherein the immunostimulatory oligonucleotide is a CpG containing ODN, and wherein the adjuvant formulation is a water-in-oil (W/O) emulsion. The adjuvant may comprise a saponin, a sterol, a quaternary ammonium compound, a polymer, and an ORN/ODN. In some embodiments, the saponin is Quil A or a purified faction thereof, the sterol is cholesterol, the quaternary ammonium compound is dimethyl dioctadecyl ammonium bromide (DDA), the polymer is polyacrylic acid, and the ORN/ODN is a CpG-containing oligonucleotide. The saponin may be present in an amount of about 1 μg to about 5,000 μg per dose, the sterol may be present in an amount of about 1 μg to about 5,000 μg per dose, the quaternary ammonium compound may be present in an amount of about 1 μg to about 5,000 μg per dose, and the polymer may be present in an amount of about 0.0001% v/v to about 75% v/v. The adjuvant may further comprise a glycolipid such as, e.g., N-(2-deoxy-2-L-leucylamino-β-D-glucopyranosyl)-N-octadecyldodecanamide acetate. In some embodiments, the adjuvant comprises a triterpenoid saponin, a sterol, a quaternary ammonium compound, and a polyacrylic acid polymer. In some embodiments, the saponin is Quil A or a purified fraction thereof, the sterol is cholesterol, and the quaternary ammonium compound is dimethyl dioctadecyl ammonium bromide (DDA). In some embodiments, wherein the saponin is present in an amount of about 1 mg to about 5,000 mg per dose, the sterol is present in an amount of about 1 mg to about 5,000 mg per dose, the quaternary ammonium compound is present in an amount of about 1 mg to about 5,000 mg per dose, and the polyacrylic acid polymer is present in an amount of about 0.0001% v/v to about 75% v/v. In some embodiments, the adjuvant comprises or is a water-in-oil emulsion. The water-in-oil emulsion may comprise an oily phase and an aqueous phase, a polycationic carrier (e.g., DEAE dextran), and a CpG-containing immunostimulatory oligonucleotide. The composition may further comprise an aluminum hydroxide gel. In some embodiments, the polycationic carrier is DEAE dextran. The composition may comprise or be an emulsion or an oil-in-water (O/W) emulsion. In some embodiments, the emulsion comprises an aqueous phase that comprises an alkyl-polyacrylic acid (alkyl-PAA) or both an acrylic polymer and dimethyl dioctadecyl ammonium bromide (DDA). In some embodiments, the aqueous phase of the oil-in-water emulsion comprises dimethyl dioctadecyl ammonium bromide (DDA) and an alkyl-polyacrylic acid (alkyl-PAA). In some embodiments, the alkyl-PAA is decyl-PAA, octyl-PAA, butyl-PAA, or methyl-PA. In some embodiments, the acrylic polymer is a polymer of acrylic acid crosslinked with polyallyl sucrose. The composition may comprise or be a water-in-oil (W/O) emulsion comprising a non-mineral oil and a emulsifier. In some embodiments, the emulsifier is a mannide mono-oleate emulsifier. In some embodiments, the adjuvant is MF59, AS01, AS02, AS03, AS04, Virosomes, CAF01, CAF04, CAF05, an acrylic polymer/DDA emulsion, a CpG/DEAE emulsion, a saponin/cholesterol/DDA adjuvant, or a polyacrylic acid polymer emulsion.

In some embodiments, the immunogenic composition comprises at least 2, 3, 4, 5, or all of TRP153, TRP36, TRP140, TRP28, TRP95, and TRP19. In some embodiments, the composition comprises (TRP153 and TRP36), (TRP153 and TRP140), (TRP153 and TRP28), (TRP153 and TRP95), (TRP36 and TRP140), (TRP36 and TRP28), (TRP36 and TRP95), (TRP140 and TRP28), (TRP140 and TRP95), (TRP28 and TRP95), (TRP19 and TRP153), (TRP19 and TRP36), (TRP19 and TRP140), (TRP19 and TRP28), (TRP19 and TRP95), (TRP120 and TRP153), (TRP120 and TRP36), (TRP120 and TRP140), (TRP120 and TRP28), (TRP120 and TRP95), or (TRP120 and TRP19). In some embodiments, the composition comprises TRP120, TRP140, and TRP36. In some embodiments, the composition comprises TRP140, TRP36, and TRP19. The composition may further comprise an *E. canis* bacterin. The *E. canis* bacterin may be a heat-inactivated or chemically-inactivated bacterin. In some embodiments, the chemically-inactivated bacterin was inactivated with formaldehyde, formalin, bi-ethylene amine, radiation, ultraviolet light, beta-propiolactone treatment, or formaldehyde. In some embodiments, the composition comprises: (SEQ ID NO:2 and at least one of (SEQ ID NOs:3-11 or 16)), (SEQ ID NO:2 and at least one of SEQ ID NOs:12-13), (SEQ ID NO:2 and SEQ ID NO:14), (at least one of (SEQ ID NOs:3-11 or 16) and at least one of SEQ ID NOs:12-13), (at least one of (SEQ ID NOs:3-11 or 16) and SEQ ID NO:14), (at least one of SEQ ID NOs:12-13 and SEQ ID NO:14), (SEQ ID NO:1 and SEQ ID NO:2), (SEQ ID NO:1 and at least one of (SEQ ID NOs:3-11 or 16)), (SEQ ID NO:1 and at least one of SEQ ID NOs:12-13), (SEQ ID NO:1 and SEQ ID NO: 14), (SEQ ID NO: 15 and SEQ ID NO:2), (SEQ ID NO: 15 and at least one of (SEQ ID NOs:3-11 or 16)), (SEQ ID NO: 15 and at least one of SEQ ID NOs:12-13), (SEQ ID NO: 15 and SEQ ID NO:14), or (SEQ ID NO: 15 and SEQ ID NO: 1). In some embodiments, the composition comprises: SEQ ID NO:15, SEQ ID NO:14, and (any one of SEQ ID NOs:3-11 or 16). In some embodiments, the composition comprises SEQ ID NO:14, SEQ ID NO:15, and SEQ ID NO:1. The composition may further comprise an *E. canis* bacterin. The *E. canis* bacterin may be a heat-inactivated or chemically-inactivated bacterin. In some embodiments, the chemically-inactivated bacterin was inactivated with formaldehyde, formalin, bi-ethylene amine, radiation, ultraviolet light, beta-propiolactone treatment, or formaldehyde. In some embodiments, the composition comprises an *E. canis* bacterin. The *E. canis* bacterin may be a heat-inactivated or chemically-inactivated bacterin. In some embodiments, the chemically-inactivated bacterin was inactivated with formaldehyde, formalin, bi-ethylene amine, radiation, ultraviolet light, beta-propiolactone treatment, or formaldehyde.

Another aspect of the present invention relates to a method of diagnosing exposure to or infection by *Ehrlicia* or *E. canis*, comprising: a) obtaining a biological sample from a mammalian subject, and b) testing the biological sample for immunoreactivity to TRP120, TRP140, and/or TRP36, or a peptide thereof, such as any of SEQ ID NOs: 3-11, 14, 15, or 16; wherein immunoreactivity to TRP120, TRP140, and/or TRP36 indicates that subject has been exposed to or infected by *Ehrlichia* or *E. canis*. In some embodiments, the mammalian subject is a dog. In some embodiments, the method comprises testing the biological sample for immunoreactivity to TRP120 and TRP36, or an immunoreactive peptide thereof, such as any of SEQ ID NOs: 3-11, 14, or 16. In some embodiments, the method comprises testing the biological sample for immunoreactivity to TRP120, TRP140, and TRP36, or an immunoreactive peptide thereof, such as any of SEQ ID NOs: 3-11, 14, 15, or 16. In some embodiments, the method further comprises a method of treating the mammalian subject, and wherein the mammalian subject is administered a pharmacologically relevant or therapeutically relevant amount of an antibiotic such as, e.g., doxycycline.

Yet another aspect of the present invention relates to a method of inducing an immune response in a mammalian subject comprising administering to the subject a pharmaceutically relevant amount of an immunogenic composition described above or herein. The immunogenic composition may comprise an adjuvant. In some embodiments, the adjuvant comprises a triterpenoid saponin (e.g., Quil A), a sterol (e.g., cholesterol), and an immunostimulatory oligonucleotide (e.g., a CpG-containing ODN). In some embodiments, the triterpenoid saponin is Quil A, the sterol is cholesterol, and the immunostimulatory oligonucleotide is a CpG-containing ODN. In some embodiments, the CpG-containing ODN is 5' JU*C-G*T*C*G*A*C*G*A*T*C*G*G*C*G*G*C*C*G*C*C*G*T 3' (SEQ ID NO:17), wherein "*" refers to a phosphorothioate bond, "-" refers to a phosphodiester bond, and "JU" refers to 5'-Iodo-2'-deoxyuridine. In some embodiments, the immunogenic composition comprises at least one, at least two, or all of TRP140, TRP36, and/or TRP19. The immunogenic composition may comprise a chimeric protein comprising 1, 2, or all of TRP140, TRP36, and/or TRP19. In some embodiments, the immunogenic composition comprises a polypeptide comprising 1, 2, or all of SEQ ID NO:1, SEQ ID NO:3, and/or SEQ ID NO:14. The immunogenic composition may comprise an adjuvant and 1, 2, or all of TRP140, TRP36, and/or TRP19. The method may further comprises administering a second immunogenic composition to the subject, wherein the second immunogenic composition comprises an *Ehrlichia* bacterin (e.g., an *E. canis* bacterin). The second immunogenic composition may comprises an adjuvant, preferably wherein the adjuvant comprises a triterpenoid saponin (e.g., Quil A), a sterol (e.g., cholesterol), and an immunostimulatory oligonucleotide (a CpG-containing ODN). In some embodiments, the adjuvant in the second immunogenic composition comprises Quil A, cholesterol, and a CpG-containing ODN. In some embodiments, the CpG-containing ODN is 5' JU*C-G*T*C*G*A*C*G*A*T*C*G*G*C*G*G*C*C*G*C*C*G*T 3' (SEQ ID NO:17), wherein "*" refers to a phosphorothioate bond, "-" refers to a phosphodiester bond, and "JU" refers to 5'-Iodo-2'-deoxyuridine. In some embodiments, the mammalian subject is a dog.

In some embodiments, the adjuvant may comprise or consist of an immunologically active saponin fraction from the bark of *Quillaja saponaria*. The saponin may be, for example, Quil A, or another purified or partially-purified saponin preparation, which can be obtained commercially. Quil A is commercially available, e.g., from E. M. Sergeant Pulp & Chemical Company (Clifton, NJ, USA). The adjuvant may comprise or consist of QS-7, QS-17, QS-18, and QS-21. QS-7, QS-17, QS-18, and QS-21 are also commercially available, e.g., from Antigenics (Framingham, Massachusetts, USA). The saponin extracts can be used as mixtures in the adjuvant, or purified individual components such as QS-7, QS-17, QS-18, and QS-21 can be included in the adjuvant. In some embodiments, the Quil A is at least about 85% pure. In other embodiments, the Quil A is at least about 90%, 91%, 92%, 93%, 94%, 95%, 96%, 97%, 98%, or about 99% pure.

The adjuvant may advantageously include a P-class immunostimulatory oligonucleotide, more preferably a modified P-class immunostimulatory oligonucleotides. P-class immunostimulatory oligonucleotides are CpG oligonucleotides that include at least one palindrome, typically 6-20 nucleotides in length. In some preferred embodiments, the P-Class oligonucleotide can spontaneously self-assemble into a concatamer, either in vitro and/or in vivo. P-Class oligonucleotides are individually single-stranded, but the presence of palindromes allows for formation of concatamers or stem-and-loop structures between multiple P-Class oligonucleotides (e.g., multiple P-Class oligonucleotides having the same nucleotide sequence). In some embodiments, P-class immunostimulatory oligonucleotides is between 19 and 100 nucleotides in length, e.g., 19-30 nucleotides, 30-40 nucleotides, 40-50 nucleotides, 50-60 nucleotides, 60-70 nucleotides, 70-80 nucleotides, 80-90 nucleotides, 90-100 nucleotides, or any range derivable therein.

In some preferred embodiments, the immunostimulatory oligonucleotide contains a 5' TLR activation domain and at least two palindromic regions, e.g.: a first palindromic region that is a 5' palindromic region of at least 6 nucleotides in length, and connected to second palindromic region that is a 3' palindromic region of at least 8 nucleotides in length, wherein the first palindromic region and the second palindromic regions are connected directly or indirectly (e.g., via a spacer). TLR-9 activating motifs are known and include, without limitation, TCG, TTCG, TTTCG, TYpR, TTYpR, TTTYpR, UCG, UUCG, UUUCG, TTT, and TTTT. The 5' TLR area may be completely or partially included into the 5' palindromic region, or may be upstream of the 5' palindromic region. The 3' palindrome or the 3' complementary area is, in certain embodiments, at least 8 bases long and is generally rich in C and G.

The P-class immunostimulatory oligonucleotide(s) may be modified according to techniques known in the art. For example, J-modification can be used to generate iodo-modified nucleotides. E-modification can be used to generate ethyl-modified nucleotide(s). In some embodiments, the immunostimulatory oligonucleotide is an E-modified P-class immunostimulatory oligonucleotides. E-modified P-class immunostimulatory oligonucleotides are P-class immunostimulatory oligonucleotides that include at least one nucleotide (preferably the 5' nucleotide) that is ethylated. Additional modifications that can be used include attachment of 6-nitro-benzimidazol, O-methylation, modification with proynyl-dU, inosine modification, and/or 2-bromovinyl attachment (preferably to a uridine).

The P-class immunostimulatory oligonucleotides may also contain a modified internucleotide linkage, including, without limitation, phosphodiester linkages and phosphorothioate linkages. The oligonucleotides described herein may be synthesized, produced recombinantly, or obtained from a commercial source.

Sterols suitable for inclusion in the adjuvant include β-sitosterol, stigmasterol, ergosterol, ergocalciferol, and/or cholesterol. These sterols are well-known in the art and can be purchased commercially. For example, cholesterol is disclosed in the Merck Index, 12th Ed., p. 369. The amount of sterol(s) included in the adjuvant compositions can depend upon the nature of the sterol used. In some embodiments, the sterol is included in the adjuvant in an amount of about 1 μg to about 5,000 μg per ml. They also are used in an amount of about 1 μg to about 4,000 μg per ml; about 1 μg to about 3,000 μg per ml; about 1 μg to about 2,000 μg per ml; and about 1 μg to about 1,000 μg per ml. They are also used in an amount of about 5 μg to about 750 μg per ml; about 5 μg to about 500 μg per ml; about 5 μg to about 200 μg per ml; about 5 μg to about 100 μg per ml; about 15 μg to about 100 μg per ml; and about 30 μg to about 75 μg per ml.

In certain embodiments, the adjuvant can comprise or consist of a sterol (e.g., cholesterol), a saponin (e.g., Quil-A), and an immunostimulatory oligonucleotide (e.g., a CpG oligonucleotide, and/or a P-class immunostimulatory oligonucleotide). In various embodiments, it is anticipated that the adjuvant may comprise: (a sterol and a saponin), (a saponin and an immunostimulatory oligonucleotide), or (a sterol and an immunostimulatory oligonucleotide). The preparation of the adjuvant containing the saponin and the sterol according to the instant invention is within the ordinary skill in the art. For example, an aqueous mixture can be prepared that comprises an antigenic protein or peptide as described herein (e.g., one or more antigenic peptides from TRP153, TRP36, TRP140, TRP28, TRP95, TRP 19, and/or TRP120; optionally further comprising an *E. canis* bacterin or an *E. chaffeensis* bacterin), the P-class immunostimulatory oligonucleotide, and the saponin. The sterol can then be gradually or dropwise added to the mixture.

"Bacterin" as used herein refers to one or more killed bacteria which may be used as a component of a vaccine or immunogenic composition. The bacterin may be comprised in a suspension. In some preferred embodiments, the bacterin is a heat-inactivated *Ehrlichia* (e.g., a heat-inactivated *E. canis*) or a chemically-inactivated *Ehrlichia* (e.g., a chemically-inactivated *E. canis*).

"Adjuvant" as used herein refers to any substance that increases the humoral or cellular immune response to an antigen. In some embodiments, Adjuvants be used to both allow for the controlled release of antigens from the injection site of a vaccine and stimulate the immune system of the subject receiving the vaccine composition.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

The present invention, in some aspects, overcomes limitations in the prior art by providing new compositions and methods that may be used to generate an immune response against an *Ehrlichia* such as *Ehrlichia canis* (*E. canis*). In some embodiments, the composition contains at least two *E. canis* proteins or immunogenic peptides and an adjuvant, as described herein. Related methods for generating an immune response against *E. canis* are also provided. In some aspects, it is anticipated that inclusion of an *E. canis* protein or immunogenic peptide in combination with an *E. canis* bacterin and/or an adjuvant may synergistically improve the immune or protective immune response in a mammalian subject such as, e.g., a dog.

I. *EHRLICHIA CANIS* IMMUNOGENIC PROTEINS AND PEPTIDES

In some aspects, an immunogenic composition as disclosed herein may comprise at least two *E. canis* immunogenic proteins or peptides and an adjuvant. For example, the immunogenic composition may comprise at least two *E. canis* immunogenic proteins and an adjuvant. In some embodiments, the immunogenic composition comprises one *E. canis* protein, one *E. canis* immunogenic peptide (e.g., the immunogenic peptide may be comprised within a peptide or polypeptide), and an adjuvant. In some embodiments, the immunogenic composition comprises at least two *E. canis* immunogenic peptide (e.g., the immunogenic peptide may be comprised within a peptide or polypeptide), and an adjuvant.

In some embodiments, the *Ehrlichia* (e.g., *E. canis*) immunogenic protein is TRP153 (e.g., also called gp153 as described in U.S. Pat. No. 7,204,992), TRP36 (e.g., also called gp36 as described in U.S. Pat. No. 9,645,148), TRP140 (e.g., also called p140 as described in U.S. Pat. No. 9,250,240), TRP28 (e.g., also called p28 as McBride et al. Gene. 2000 Aug. 22; 254(1-2):245-52), TRP95 (e.g., McBride et al., Infect Immun 2011 August; 79(8):3178-87), TRP19 (e.g., Aguiar et al. Ticks Tick Borne Dis. 2016 February; 7(1):142-145), or TRP120 (e.g., Zhu et al., Infect Immun 2011 November; 79(11):4370-81), or one or more peptides comprising or consisting of an immunogenic region thereof; in some embodiments, a vaccine composition as disclosed herein may comprise 1, 2, 3, 4, or more of these immunogenic proteins and an adjuvant as described herein. For example, in some embodiments an immunogenic composition comprises (TRP140, TRP36, and TRP19) and/or immunoreactive peptides thereof.

In some embodiments, the *Ehrlichia* immunogenic protein comprises or consists an immunogenic region of an *E. canis* protein. In some embodiments, the *E. canis* immunogenic protein comprises or consists of a peptide of Table 1. In some embodiments, a vaccine composition includes an adjuvant and 1, 2, 3, 4, 5, or more of the immunogenic peptides of Table 1, which may optionally be comprised in a peptide or polypeptide.

TABLE 1

| Ehrlichia immunogenic peptides. | | | |
|---|---|---|---|
| Immunogenic Peptide | Sequence | | Species |
| TRP19 | HFTGPTSFEVNLSE EEKMELQEVS | SEQ ID NO: 1 | E. canis |
| P28 | AKEEKNATAKTFQLK GDWDGA | SEQ ID NO: 2 | E. canis |
| TRP36R1 | TEDSVSAPA | SEQ ID NO: 3 | E. canis |
| TRP36R2 | ASVVPEAE | SEQ ID NO: 4 | E. canis |
| TRP36R3 | TEDPVSATA | SEQ ID NO: 5 | E. canis |
| TRP36R1-R2-R3 | TEDSVSAPA ASVVPEAE TEDPVSATA | SEQ ID NO: 6 | |
| TRP36R1-R3-R2 | TEDSVSAPA TEDPVSATA ASVVPEAE | SEQ ID NO: 7 | |

TABLE 1-continued

_Ehrlichia immunogenic peptides._

| Immunogenic Peptide | Sequence | | Species |
|---|---|---|---|
| TRP36R2-R1-R3 | ASVVPEAE TEDSVSAPA TEDPVSATA | SEQ ID NO: 8 | |
| TRP36R2-R3-R1 | ASVVPEAE TEDPVSATA TEDSVSAPA | SEQ ID NO: 9 | |
| TRP36R3-R1-R2 | TEDPVSATA TEDSVSAPA ASVVPEAE | SEQ ID NO: 10 | |
| TRP36R3-R2-R1 | TEDPVSATA ASVVPEAE TEDSVSAPA | SEQ ID NO: 11 | |
| TRP95R | DDSKLPVIKVEDKSKLQDT KDKKR | SEQ ID NO: 12 | _E. canis_ |
| TRP95C | KKIKEYDEDYTITYYYDDD | SEQ ID NO: 13 | _E. canis_ |
| TRP140 | EHSSSEVGEKVSETSKEEN TPEVKA | SEQ ID NO: 14 | _E. canis_ |
| TRP120 | SKVEQEETNPEVLIKDLQD VAS | SEQ ID NO: 15 | _E. chaffeensis_ |
| TRP36CO | EASVVPAAEAPQPAQQTED EFFSDGIEA | SEQ ID NO: 16 | _E. canis_ |

In some embodiments, an immunogenic composition as described herein comprises TRP140 (or a peptide comprising or consisting of SEQ ID NO:14), TRP36 (or a peptide comprising or consisting of any of SEQ ID NOs:3-11 or 16), and an adjuvant. In some embodiments, an immunogenic composition as described herein comprises TRP140 (or a peptide comprising or consisting of SEQ ID NO:14), TRP36 (or a peptide comprising or consisting of any of SEQ ID NOs:3-11 or 16), TRP19 (or a peptide comprising or consisting of SEQ ID NO: 1), TRP120 (or a peptide comprising or consisting of any of SEQ ID NO: 15), and an adjuvant. In some embodiments, the immunogenic composition does not comprise TRP19. In some embodiments, an immunogenic composition as described herein comprises: TRP140 (or a peptide comprising or consisting of SEQ ID NO:14); TRP36 (or a peptide comprising or consisting of any of SEQ ID NOs:3-11 or 16); TRP95 (or a peptide comprising or consisting of either or both of SEQ ID NOs:12-13), and an adjuvant. In some embodiments, the immunogenic composition comprises 1, 2, 3, 4, or all of TRP153, TRP36, TRP140, TRP28, and/or TRP95, and the immunogenic composition may further comprise an adjuvant, as described herein. For example, the immunogenic composition may comprise: (TRP153 and TRP36), (TRP153 and TRP140), (TRP153 and TRP28), (TRP153 and TRP95), (TRP36 and TRP140), (TRP36 and TRP28), (TRP36 and TRP95), (TRP140 and TRP28), (TRP140 and TRP95), (TRP28 and TRP95), (TRP19 and TRP153), (TRP19 and TRP36), (TRP19 and TRP140), (TRP19 and TRP28), (TRP19 and TRP95), (TRP120 and TRP153), (TRP120 and TRP36), (TRP120 and TRP140), (TRP120 and TRP28), (TRP120 and TRP95), or (TRP120 and TRP19); wherein the immunogenic composition preferably comprises an adjuvant.

II. _E. CANIS_ BACTERIN

In some embodiments, an immunogenic or vaccine composition as disclosed herein comprises an _Ehrlichia_ bacterin, preferably an _E. canis_ bacterin. An _E. canis_ bacterin may be prepared by heat-inactivating or chemically-inactivating _E. canis_ bacteria.

A variety of methods may be used to generate _E. canis_ bacterin. For example, the bacterin may be inactivated by heat or psoralen in the presence of ultraviolet light. The effective immunizing amount of the inactivated _E. canis_ bacterin can vary depending upon the chosen strain or strains. It is anticipated that any amount of _E. canis_ bacterin, alone or in combination with wither (i) other _E. canis_ immunogenic proteins or peptides (e.g., as described in Table 1), and/or (ii) adjuvant(s), sufficient to evoke a protective immune response may be used in various embodiments. In some embodiments, a dosage unit comprising at least about $1\times10^4$ TCID$_{50}$ inactivated _E. canis_ bacterin can be used. Additional methods that may be used to generate _E. canis_ bacterin include, but are not limited to, treatment of _E. canis_ with heat, formaldehyde, formalin, bi-ethylene amine, radiation, and beta-propiolactone treatment. It is anticipated that _E. canis_ bacterin may be inactivated by any suitable method available. Additional methods that may be used to generate an _Ehrlichia_ or _E. canis_ bacterin include those described, e.g., in WO2005087803, EP2433646, Vega et al. (_Vaccine_ (2007) 25:519-525), or Stuen et al. (_Acta Vet Scand_ (2015):57:40).

In some embodiments, the _E. canis_ bacterin comprises inactivated crude antigen based on inactivated _E. canis_ bacteria. For example, in some embodiments, frozen buffy coat (e.g., 10 ml frozen buffy coat) containing _E. canis_ may be obtained, and the material was inactivated using 0.3% formaldehyde for 48 h at room temperature. Thereafter, the material can tested for lack of infectivity by in vitro methods or by using an in vivo animal model. Methods for inactivating bacteria using formaldehyde are further described in Tollersrud et al. (_Vaccine_ (2001) 19:3896-3903). The resulting _E. canis_ bacterin can be included with (i) 1, 2, 3, or more _E. canis_ immunogenic proteins or peptides (e.g., as described in Table 1) and/or (ii) an adjuvant, to form an immunogenic or vaccine composition. For example, the inactivated _E. canis_ bacterin may be prepared as a suspension and then included in an emulsion adjuvant, e.g., as described below.

III. ADJUVANTS

In some aspects, an immunogenic or vaccine composition as disclosed herein (e.g., containing at least 2, 3, 4, 5, 6, or more of the immunogenic peptides or proteins of TRP153, TRP36, TRP140, HSP, TRP28, TRP19, TRP140 and/or TRP120, or a peptide or polypeptide comprising or consisting of a peptide of Table 1) contains an adjuvant. A variety of adjuvants are known that can be included. For example, adjuvants such as MF59, AS01, AS02, AS03, AS04, Virosomes, CAF01, CAF04, CAF05, Montanide ISA™ 720, or Montanide ISA™ 51 (e.g., Bonam et al., Trends in Pharmacological Sciences (2017) 38(9): 771-778).

In some embodiments, the immunogenic or vaccine composition includes an adjuvant comprising a triterpenoid, sterol, immunomodulator, polymer, and/or Th2 stimulator. For example, in some embodiments the adjuvant comprises DEAE Dextran, an immunostimulatory oligonucleotide, and oil (e.g., a light mineral oil), wherein the immunostimulatory oligonucleotide is a CpG containing ODN, and wherein the adjuvant formulation is a water-in-oil (W/O) emulsion. The vaccine adjuvant may comprise an _E. canis_ bacterin (such as a heat-inactivated _E. canis_) and/or 1, 2, 3, or more of the immunogenic _E. canis_ proteins or peptides of Table 1 or as disclosed herein. In some embodiments, the immunogenic or vaccine composition includes an antigen component and an adjuvant formulation comprising a saponin (e.g., present in an amount of about 1 μg to about 5,000 μg per dose), a sterol (e.g., present in an amount of about 1 μg to about 5,000 μg per dose), a quaternary ammonium compound (e.g., present in an amount of about 1 μg to about 5,000 μg per dose), a polymer (e.g., present in an amount of about 0.0001% v/v to about 75% v/v.), and an ORN/ODN; the saponin may be Quil A or a purified faction thereof, the sterol may be cholesterol, the quaternary ammonium compound may be dimethyl dioctadecyl ammonium bromide (DDA), the polymer may be polyacrylic acid, and the ORN/ODN may be a CpG. The adjuvant may comprise a glycolipid, such N-(2-deoxy-2-L-leucylamino-β-D-glucopyranosyl)-N-octadecyl-dodecanamide acetate. The adjuvant may comprise an immunostimulatory oligonucleotide, a polyacrylic acid polymer and at least two of the following: (a) dimethyl dioctadecyl ammonium bromide (DDA); (b) a sterol; and/or (c) N-(2-deoxy-2-L-leucylamino-β-D-glucopyranosyl)-N-octadecyldodecanamide acetate. For example, the vaccine composition may comprise an adjuvant as described, e.g., in U.S. Pat. Nos. 10,238,736, 8,580,280, or US Publication 2019/0008953.

In some embodiments, immunogenic or vaccine composition includes an antigen component and an adjuvant formulation comprising a triterpenoid saponin, a sterol, a quaternary ammonium compound, and a polyacrylic acid polymer, wherein the antigen component comprises or consists of a *E. canis* bacterin (such as a heat-inactivated *E. canis*) and/or an *E. canis* immunogenic protein or peptide (e.g., 1, 2, 3, or more *E. canis* proteins described herein and/or 1, 2, 3, or more peptides of Table 1). In some embodiments, the saponin is present in an amount of about 1 mg to about 5,000 mg per dose, the sterol is present in an amount of about 1 mg to about 5,000 mg per dose, the quaternary ammonium compound is present in an amount of about 1 mg to about 5,000 mg per dose, and the polyacrylic acid polymer is present in an amount of about 0.0001% v/v to about 75% v/v. For example, the vaccine composition may comprise an adjuvant as described, e.g., in U.S. Pat. No. 9,662,385.

In some aspects, an immunogenic or vaccine composition as disclosed herein comprises an oil-based adjuvant comprising an *E. canis* bacterin (such as a heat-inactivated *E. canis*) and/or 1, 2, 3, or more *E. canis* immunogenic proteins or peptides as described herein. For example, the adjuvant formulation may comprise an oily phase and an aqueous phase, a polycationic carrier (e.g., DEAE dextran), and a CpG containing immunostimulatory oligonucleotide, wherein the vaccine is a water-in-oil emulsion. The adjuvant may optionally further comprise an aluminum hydroxide gel. In some embodiments, the CpG containing immunostimulatory oligonucleotide is present in the amount of about 50 to about 400 μg per dose and DEAE Dextran is present in the amount of about 10 to about 300 mg per dose. The adjuvant formulation may comprise an immunostimulating oligonucleotide, polycationic carrier, sterol, saponin, quaternary amine, TLR-3 agonist, glycolipid, and/or MPL-A (or an analog thereof) in an oil emulsion. For example, the vaccine composition may comprise an adjuvant as described, e.g., in U.S. Pat. No. 10,117,921 or US 2019/0038737.

In some embodiments, the immunogenic composition is an emulsion comprising (i) an *E. canis* bacterin (such as a heat-inactivated *E. canis*), and/or (ii) 1, 2, 3, 4, or more *E. canis* immunogenic protein(s) or peptide(s) as described herein (e.g., in Table 1). For example, the emulsion composition may comprise an adjuvant, such as acrylic polymer and/or dimethyl dioctadecyl ammonium bromide (DDA), in the aqueous phase. The emulsion can be prepared, in some embodiments, by mixing an aqueous phase containing the antigen (e.g., an *E. canis* bacterin such as a heat-inactivated *E. canis*, and/or 1, 2, 3, or more *E. canis* immunogenic protein or peptide as described herein) and adjuvant with an oil phase in the presence of an emulsifier. In some embodiments, the adjuvant component comprises an oil-in-water emulsion, wherein the aqueous phase of the oil-in-water emulsion comprises dimethyl dioctadecyl ammonium bromide (DDA) and/or an alkyl-polyacrylic acid (alkyl-PAA). In some embodiments, the oil in the oil-in-water emulsion is mineral oil, a terpene oil, soybean oil, olive oil, or a propylene glycol derivative. The adjuvant may further comprise the adjuvant component further comprises CpG DNA, a lipopolysaccharide, and/or monophosphoryl lipid A. The vaccine may further comprise one or more emulsifiers. For example, the vaccine composition may comprise an adjuvant as described, e.g., in U.S. Pat. No. 9,545,439 or U.S. Pat. No. 8,980,288.

The adjuvant may be a liposome or emulsion formulation. The liposomes may be unilamellar, multilamellar, or multivesicular. In some embodiments, the an immunogenic or vaccine composition comprises a lipid or lipid-containing adjuvant. In some embodiments, the liposomes are cationic liposomes. In various embodiments, adjuvants such as MF59 (e.g., Calabro et al. (2013) *Vaccine* 31: 3363-3369), AS01 (Didierlaurent, et al. (2014) *J. Immunol.* 193, 1920-1930), AS02 (Garcon and Van Mechelen (2011) *Expert Rev. Vaccines* 10, 471-486), AS03 (Morel, S. et al. (2011) *Vaccine* 29, 2461-2473), AS04 (Didierlaurent, et al. (2009) *J. Immunol.* 183: 6186-6197.), Virosomes (Künzi, et al. (2009) *Vaccine* 27, 3561-3567), CAF01 (Tandrup Schmidt, et al. (2016) *Pharmaceutics* 8, 7.), CAF04 (Billeskov, et al. (2016) *PLoS One* 11, e0161217), CAF05 (Billeskov, et al. (2016) *PLoS One* 11, e0161217), Montanide ISA™ 720 (Aucouturier, et al. (2002) *Expert Rev. Vaccines* 1, 111-118), or Montanide ISA™ 51 (Aucouturier, et al. (2002) *Expert Rev. Vaccines* 1, 111-118) can be used. Table 2 provides a listing of example adjuvant containing formulations that can be used in various embodiments.

TABLE 2

| Example adjuvant containing formulations | |
| --- | --- |
| Adjuvant | Composition |
| MF59 | Squalene, Span 85, Tween 80, and citrate buffer |
| AS01 | Liposomes containing 3-O-desacyl-4'-monophosphoryl lipid A (MPLA) and QS21 |
| AS02 | Oil-in-water (O/W) emulsion containing MPLA and the saponin QS21 |
| AS03 | α-tocopherol, squalene, polysorbate 80, and PBS |
| AS04 | Contains MPLA adsorbed onto a particulate form of aluminum salt |

TABLE 2-continued

| Example adjuvant containing formulations | |
|---|---|
| Adjuvant | Composition |
| Virosomes | Contain inactivated virus |
| CAF01 | Cationic liposomal vehicle containing dimethyl dioctadecyl-ammonium (DDA) with a glycolipid immunostimulator (TDB) |
| CAF04 | Cationic liposomal vehicle containing DDA with monomycoloyl glycerol analog (MMG) |
| CAF05 | Cationic liposomal vehicle containing DDA with the immunostimulators TDB and poly (I:C) |
| Montanide ISA ™ 720 | Water-in-oil (W/O) emulsion containing non-mineral oil with mannide mono-oleate family emulsifier |
| Montanide ISA ™ 51 | W/O emulsion containing mineral oil with mannide mono-oleate family emulsifier |
| Acrylic polymer/DDA emulsions | Oil-in-water emulsion comprises dimethyl dioctadecyl ammonium bromide (DDA) and/or an alkyl-polyacrylic acid (alkyl-PAA); e.g., see U.S. Pat. No. 9,545,439 or U.S. Pat. No. 8,980,288. |
| CpG/DEAE emulsions | Emulsions comprising a polycationic carrier (e.g., DEAE dextran) and a CpG containing immunostimulatory oligonucleotide; e.g., see U.S. Pat. No. 10,117,921 or US 2019/0038737. |
| Saponin/cholesterol/ DDA adjuvants | Saponin (e.g., Quil A), cholesterol, DDA, a polyacrylic acid; e.g., a triterpenoid saponin, a sterol, a quaternary ammonium compound, and a polyacrylic acid polymer; e.g., see U.S. Pat. No. 9,662,385. |
| Polyacrylic acid polymer emulsions | Water-in-oil (W/O) emulsions, DEAE Dextran, immunostimulatory oligonucleotide (e.g., a CpG containing ODN), a sterol, N-(2-deoxy-2-L-leucylamino-$\beta$-D-glucopyranosyl)-N-octadecyldodecanamide acetate, and/or a polyacrylic acid polymer; e.g., see U.S. Pat. No. 10,238,736, U.S. Pat. No. 8,580,280, or US Publication 2019/0008953. |

IV. IMMUNOGENIC AND VACCINE COMPOSITIONS

In some embodiments, 1, 2, 3, 4, or more of the immunogenic proteins or peptides disclosed herein may be included in a pharmaceutical composition, optionally with an *E. canis* bacterin and/or an adjuvant, e.g., as described herein. The pharmaceutical composition may be administered to a mammalian subject, such as a dog, e.g., to induce a protective immune response against an *Ehrlichia* such as *E. canis*. In some embodiments the pharmaceutical composition is used as a vaccine.

In select embodiments, the immunoreactive composition or vaccine composition is administered to a subject (e.g., a dog) to induce a protective immune response in the subject that may substantially prevent or ameliorate infection in the subject by *Ehrlichia* canis. A vaccine composition for pharmaceutical use in a subject may comprise an immunoreactive polypeptide of 2, 3, 4, or more of the immunogenic proteins or peptides disclosed herein, an adjuvant as disclosed herein, and a pharmaceutically acceptable carrier.

The phrases "pharmaceutical," "pharmaceutically acceptable," or "pharmacologically acceptable" refers to molecular entities and compositions that do not produce an adverse, allergic or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1289-1329, 1990, incorporated herein by reference). Except insofar as any conventional carrier is incompatible with the active ingredient, its use in the vaccine compositions of the present disclosure is contemplated.

As used herein, a "protective immune response" refers to a response by the immune system of a mammalian host to an *Ehrlichia* antigen which results in increased recognition of the antigen and antibody production by the immune system of the mammalian host upon subsequent exposure to an *Ehrlichia* pathogen. A protective immune response may substantially reduce or prevent symptoms as a result of a subsequent exposure to *Ehrlichia chaffeensis* or *Ehrlichia canis*.

A person having ordinary skill in the medical arts will appreciate that the actual dosage amount of a vaccine composition administered to an animal or human patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, vaccine compositions may comprise, for example, at least about 0.1% of an ehrlichial immunoreactive polypeptide comprising a polypeptide of Formula I or a polypeptide of Table 2. In other embodiments, the an active compound may comprise between about 2% to about 75% of the weight of the unit, or between about 25% to about 60%, for example, and any range derivable therein. As with many vaccine compositions, frequency of administration, as well as dosage, will vary among members of a population of animals or humans in ways that are predictable by one skilled in the art of immunology. By way of nonlimiting example, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1-36 week period. Preferably, 3 doses are administered, at intervals of 3-4 months, and booster vaccinations may be given periodically thereafter.

In some embodiments, a "suitable dose" is an amount of an immunoreactive polypeptide that, when administered as described above, is capable of raising an immune response in an immunized patient sufficient to protect the subject from an *Ehrlichia* infection in subsequent exposures to *Ehrlichia* organisms. In general, the amount of peptide present in a suitable dose (or produced in situ by the nucleic acid in a dose) may range from about 1 pg to about 500 mg per kg of host, typically from about 10 pg to about 10 mg, preferably from about 100 pg to about 1 mg and more preferably from about 100 pg to about 100 microgram.

A vaccine composition of the present disclosure may comprise different types of carriers depending on whether it is to be administered in solid, liquid or aerosol form, and whether it needs to be sterile for such routes of administration as injection. A vaccine composition disclosed herein can be administered intramuscularly, intradermally, subcutaneously, intravenously, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subconjunctivally, intravesicularly, mucosally, intrapericardially, locally, orally, intranasally, or by inhalation, injection, infusion, continuous infusion, lavage, or localized perfusion. A vaccine composition may also be administered to a subject via a catheter, in cremes, in lipid compositions, by ballistic particulate delivery, or by other method or any combination of the forgoing as would be known to one of ordinary skill in the art (see, for example, Remington: The Science and Practice of Pharmacy, 21$^{st}$ Ed. Lippincott Williams and Wilkins, 2005, incorporated herein by reference).

While any suitable carrier known to those of ordinary skill in the art may be employed in the vaccine compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Of particular interest in an aspect of the present disclosure is a vaccine composition that may be administered by microstructured transdermal or ballistic particulate delivery. Microstructures as carriers for vaccine formulation are a desirable configuration for vaccine applications and are widely known in the art (e.g., U.S. Pat. Nos. 5,797,898, 5,770,219 and 5,783,208, and U.S. Patent Application 2005/0065463). Such a vaccine composition formulated for ballistic particulate delivery may comprise an isolated immunoreactive polypeptide of Table 1, 2, or 3 immobilized on a surface of a support substrate. In these embodiments, a support substrate can include, but is not limited to, a microcapsule, a microparticle, a microsphere, a nanocapsule, a nanoparticle, a nanosphere, or a combination thereof.

Microstructures or ballistic particles that serve as a support substrate for an ehrlichial immunoreactive polypeptide disclosed herein may be comprised of biodegradable material and non-biodegradable material, and such support substrates may be comprised of synthetic polymers, silica, lipids, carbohydrates, proteins, lectins, ionic agents, crosslinkers, and other microstructure components available in the art. Protocols and reagents for the immobilization of a peptide of the invention to a support substrate composed of such materials are widely available commercially and in the art.

In other embodiments, a vaccine composition comprises an immobilized or encapsulated immunoreactive polypeptide or peptide as disclosed herein, an adjuvant as disclosed herein, and a support substrate. In these embodiments, a support substrate can include, but is not limited to, a lipid microsphere, a lipid nanoparticle, an ethosome, a liposome, a niosome, a phospholipid, a sphingosome, a surfactant, a transferosome, an emulsion, or a combination thereof. The formation and use of liposomes and other lipid nano- and microcarrier formulations is generally known to those of ordinary skill in the art, and the use of liposomes, microparticles, nanocapsules and the like have gained widespread use in delivery of therapeutics (e.g., U.S. Pat. No. 5,741,516, specifically incorporated herein in its entirety by reference). Numerous methods of liposome and liposome-like preparations as potential drug carriers, including encapsulation of peptides, have been reviewed (U.S. Pat. Nos. 5,567,434; 5,552,157; 5,565,213; 5,738,868 and 5,795,587, each of which is specifically incorporated in its entirety by reference).

In addition to the methods of delivery described herein, a number of alternative techniques are also contemplated for administering the disclosed vaccine compositions. By way of nonlimiting example, a vaccine composition may be administered by sonophoresis (i.e., ultrasound) which has been used and described in U.S. Pat. No. 5,656,016 for enhancing the rate and efficacy of drug permeation into and through the circulatory system; intraosseous injection (U.S. Pat. No. 5,779,708), or feedback-controlled delivery (U.S. Pat. No. 5,697,899), and each of the patents in this paragraph is specifically incorporated herein in its entirety by reference.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, Bortadella pertussis or Mycobacterium tuberculosis. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N.J.). Other suitable adjuvants include alum, biodegradable microspheres, monophosphoryl lipid A and quil A.

A polypeptide may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

Sterile injectable solutions are prepared by incorporating the active peptides in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

In particular embodiments, prolonged absorption of an injectable composition can be brought about by the use in the compositions of agents delaying absorption, such as, for example, aluminum monostearate, gelatin or combinations thereof.

V. EHRLICHIA VACCINATION KITS

In some embodiments, kits are provided for vaccination of a subject (e.g., a dog) against E. canis infection that include an immunogenic polypeptide or immunogenic peptide as disclosed herein. In some embodiments, the composition may be administered to the subject to induce a protective immune response against an E. canis infection.

As appropriate to the method being performed, a kit may further comprise one or more apparatuses for delivery of a composition to a subject or for otherwise handling a composition of the invention. By way of nonlimiting example, a kit may include an apparatus that is a syringe, an eye dropper, a ballistic particle applicator (e.g., applicators disclosed in U.S. Pat. Nos. 5,797,898, 5,770,219 and 5,783, 208, and U.S. Patent Application 2005/0065463), and such like.

When reagents and/or components comprising a kit are provided in a lyophilized form (lyophilisate) or as a dry powder, the lyophilisate or powder can be reconstituted by the addition of a suitable solvent. In particular embodiments, the solvent may be a sterile, pharmaceutically acceptable buffer and/or other diluent. It is envisioned that such a solvent may also be provided as part of a kit.

When the components of a kit are provided in one and/or more liquid solutions, the liquid solution may be, by way of non-limiting example, a sterile, aqueous solution. The compositions may also be formulated into an administrative composition. In this case, the container means may itself be a syringe, pipette, topical applicator or the like, from which the formulation may be applied to an affected area of the body, injected into a subject, and/or applied to or mixed with the other components of the kit.

VI. METHODS OF PRODUCING AN IMMUNOREACTIVE POLYPEPTIDE

An immunoreactive polypeptide of the present disclosure may be produced using a variety of methods, including recombinant production of a protein from cells, in vitro transcription and translation (IVTT) methods, and/or peptide synthesis (e.g., using solid-phase synthesis).

IVTT may be used to recombinantly produce a protein using a variety of cell types (e.g., bacterial cells, mammalian cells, E. coli, yeast, and insect cells, etc.). A variety of IVTT approaches are known in the art and may be used in various embodiments. IVTT generally involves cell-free methods for production or synthesis of a protein from DNA. The cell-free system for protein production may use, e.g., E. coli extract, protozoan extracts, yeast extracts, human cell extract, wheat germ extract, mammalian extracts, extracts from cultured human cell lines, rabbit reticulocyte lysate, insect cell extract, or reconstituted and purified E. coli components. A variety of kits are commercially available including, e.g., RTS (FivePrime, San Francisco, CA), Expressway™ (Life Technologies); S30 T7 high yield (Promega), One-step human IVT (Thermo Scientific), WEPRO® (CellFree Sciences), TNT® coupled (Promega), RTS CECF (5 PRIME), TNT® Coupled (Promega), Retic lysate IVT™ (Life Technologies); TNT® T7 (Promega), EasyXpress Insect kit (Qiagen/RiN A), PURExpress® (New England Biolabs), and PURESYSTEM® (BioComber). Such methods can be used to incorporate unnatural amino acids into proteins, if desired. Cell-free expression systems that may be used in various embodiments are also described, e.g., in Zemella et al., 2015.

An isolated immunoreactive protein as disclosed herein may be produced in some embodiments using an appropriate method known in the organic chemistry arts. For example, peptides may be produced using one of the established solid-phase peptide synthesis techniques that are well known in the art. In some embodiments, peptides may be synthesized using equipment for automated peptide synthesis that is widely available from commercial suppliers such as Perkin Elmer (Foster City, CA), or the peptide may be chemically synthesized using solution-phase techniques such as those described in Carpino et al., 2003 or U.S. Patent Application 2009/0005535. In some embodiments, the peptides or shorter proteins may be synthesized, e.g., using solid-phase peptide synthesis (SPPS), t-Boc solid-phase peptide synthesis, or Fmoc solid-phase peptide synthesis.

In some embodiments, an immunoreactive protein as described herein can be recombinantly prepared from a nucleic acid encoding the polypeptide or peptide. Such a nucleic acid may be operably linked to an expression vector. By way of nonlimiting example, an immunoreactive protein may be expressed from a vector and isolated from the growth media of a host cell comprising the vector. In some embodiments, the immunoreactive protein may be produced in a cell-free system from a nucleic acid encoding the peptide.

In general, regardless of the method of preparation, the immunoreactive proteins disclosed herein are preferably prepared in a substantially pure form. Preferably, the immunoreactive proteins are at least about 80% pure, more preferably at least about 90% pure, even more preferably at least 95% pure, and most preferably at least about 99% pure.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Vaccine Efficacy Evaluation of the *Ehrlichia Canis* Bacterin and Recombinant TRP Antigens in Beagles The objective of the study was to evaluate the efficacy of an *Ehrlichia canis* bacterin vaccine, produced via different processes, in a novel adjuvant formulation consisting of Quil A, cholesterol, and CpG ODN of SEQ ID NO:17 (5'

JU*C-
G*T*C*G*A*C*G*A*T*C*G*G*C*G*G*C*C*G*C*C*
G*T 3', wherein "*" refers to a phosphorothioate bond, "-" refers to a phosphodiester bond, and "JU" refers to 5'-Iodo-2'-deoxyuridine) (QCT; each component present at 50 µg/dose) against a heterologous *Ehrlichia canis* (*E. canis*) Ebony strain challenge in dogs approximately 12 weeks of age at first vaccination. Additionally, the efficacy of vaccines containing recombinant Tandem Repeat Proteins (TRP), 19, 36 & 120 kDa in size, of *E. canis* were evaluated either as a 3-way combination vaccine, or as a (bacterin with QCT)+ (TRP antigens with QCT) co-administration combination vaccine.

Seventy-two (72) male beagles, approximately 12 weeks of age, were randomly assigned to one of six treatment groups (12 animals/treatment group) using a randomized complete block design. Treatment groups were defined as T01—Saline controls; T02—*E. canis* Sheba Whole Cell Silverson bacterin, BEI (binary ethyleneimine) inactivation+QCT; T03—*E. canis* Sheba Whole Cell Silverson bacterin, BEI inactivation+QCT; T04—[*E. canis* Sheba Whole Cell Silverson bacterin, BEI inactivation+QCT] and [TRP 140, 36, 19+QCT] (co-administered); T05—Formalin-inactivated Bacterin+QCT; and T06-TRP 140, 36, 19+QCT (Table 1).

All dogs were healthy and negative for *E. canis* by IDEXX SNAP 4Dx Plus prior to vaccination on Day 0. All animals were subcutaneously vaccinated with either placebo (saline) or Investigational Veterinary Product (IVP) on Days 0 and 28. Animals were challenged via the intravenous route with *E. canis* Ebony strain six weeks after second vaccination. Tympanic temperatures were collected daily, and all animals were observed daily for clinical signs of *E. canis* infection through the end of study (Day 134). Blood samples were collected for Complete Blood Chemistry (CBC) testing every three days post-challenge, as well as for qPCR testing, starting seven days post-challenge. Additional blood samples were collected for IDEXX SNAP® 4Dx Plus testing on Days 0, 28, 49, and 134; ELISA testing on Days 0, 28, 49, 68-70, and 134; and CMI analysis on Days 0, 35, 83, and 104.

TABLE 1

Study Design

| TRT | # Animals | Treatment | Vaccination Days* | Dose | Dose Units | Route | Challenge |
|---|---|---|---|---|---|---|---|
| T01 | 12 | Saline | 0, 28 | 1.0 | mL | SQ | Day 70 |
| T02 | 12 | *E. canis* Sheba Whole Cell Silverson bacterin (BEI inactivation) + QCT | | 1.0 | | | |
| T03 | 12 | *E. canis* Sheba Whole Cell Silverson bacterin (media-free; BEI inactivation) + QCT | | 1.0 | | | |
| T04 | 12 | [*E. canis* Sheba Whole Cell Silverson bacterin (BEI inactivation) + QCT] and [TRP 140, 36, 19 + QCT] | | 1.0 of bacterin + 1.0 of TRP | | | |
| T05 | 12 | *E. canis* Sheba Whole Cell Silverson bacterin (Formalin inactivation) + QCT | | 1.0 | | | |
| T06 | 12 | TRP 140, 36, 19 + QCT | | 1.0 | | | |

*Vaccination on Day 0 was performed over the right shoulder region. Vaccination on Day 28 was performed over the left shoulder region.

Efficacy in this study was determined based on the reduction of thrombocytopenia (platelet counts $<143\times10^3/\mu L$ and >50% reduction from baseline) and clinical disease (mainly fever) post-challenge. A vaccine effect would be confirmed if the T02, T03, T04, T05, and/or T06 treatment groups had significantly less thrombocytopenia or clinical disease after challenge compared to T01 controls.

Results

For this study, qPCR was performed on bulk antigens to standardize vaccine formulations based on inactivated bacterin genomes. Target vaccines for this study were blended at 400 µg of inactivated bacterin.

The presence of thrombocytopenia (platelet count $<143\times10^3/\mu L$) post-challenge was significantly reduced in treatment groups T02 (67%, P=0.0497), T03 (67%, P=0.0497), and T04 (58%, P=0.0141) when compared to treatment group T01 (100%). There was no significant reduction in thrombocytopenia in treatment groups T05 (75%) and T06 (83%) when compared to treatment group T01 (controls) (Tables 2 and 3).

TABLE 2

Ever-Present Thrombocytopenia by Treatment Group

| | Result | | | | |
|---|---|---|---|---|---|
| | NO | | YES | | |
| Treatment | n | (%) | n | (%) | Total |
| T01 | 0 | 0 | 12 | 100 | 12 |
| T02 | 4 | 33 | 8 | 67 | 12 |
| T03 | 4 | 33 | 8 | 67 | 12 |
| T04 | 5 | 42 | 7 | 58 | 12 |
| T05 | 3 | 25 | 9 | 75 | 12 |
| T06 | 2 | 17 | 10 | 83 | 12 |

T01—Saline control

T02—*E. canis* Sheba Whole Cell Silverson bacterin (BEI inactivation)+QCT

T03—*E. canis* Sheba Whole Cell Silverson bacterin (media-free; BEI inactivation)+QCT T04—[*E. canis* Sheba Whole Cell Silverson bacterin (BEI inactivation)+QCT]+[TRP 140, 36, 19+QCT]

T05—*E. canis* Sheba Whole Cell Silverson bacterin (Formalin inactivation)+QCT

T06—TRP 140, 36, 19+QCT

TABLE 3

Ever-Present Significance of Treatment Comparisons of Thrombocytopenia

| | Thrombocytopenia | | | | |
|---|---|---|---|---|---|
| (Platelet Counts <143 × 103/μL) | | | (Platelet Counts >50% Reduction from Baseline) | | |
| Contrast | P-value | Significance of P-value | Contrast | P-value | Significance of P-value |
| T01 vs T02 | 0.0497 | Yes | T01 vs T02 | 0.1368 | No |
| T01 vs T03 | 0.0497 | Yes | T01 vs T03 | 0.0473 | Yes |
| T01 vs T04 | 0.0141 | Yes | T01 vs T04 | 0.0132 | Yes |
| T01 vs T05 | 0.1410 | No | T01 vs T05 | 0.1368 | No |
| T01 vs T06 | 0.3264 | No | T01 vs T06 | 0.3213 | No |

T01—Saline control
T02—*E. canis* Sheba Whole Cell Silverson bacterin (BEI inactivation) + QCT
T03—*E. canis* Sheba Whole Cell Silverson bacterin (media-free; BEI inactivation) + QCT
T04—[*E. canis* Sheba Whole Cell Silverson bacterin (BEI inactivation) + QCT] + [TRP 140, 36, 19 + QCT]
T05—*E. canis* Sheba Whole Cell Silverson bacterin (Formalin inactivation) + QCT
T06—TRP 140, 36, 19 + QCT Duration of thrombocytopenia was significantly reduced in the co-administration treatment group T04 when compared to the control group T01 by both measures of thrombocytopenia. When thrombocytopenia was measured by platelet counts <143×10³/μL, the duration of thrombocytopenia for T04 was 23.08 days (LSM) compared to 47.42 days in T01 (P=0.0014). When thrombocytopenia was measured by a >50% reduction in platelet counts from baseline, the duration for T04 was 23.83 days compared to 47.92 days in T01 (P=0.0020).

All vaccinated treatment groups containing bacterin (T02-T05) had significant reduction in duration of thrombocytopenia when compared to treatment group T01 (controls). Treatment group T06, containing only the TRP antigens+adjuvant, did not have a significant reduction in duration of thrombocytopenia when compared to the control group when thrombocytopenia was defined as platelet counts >50% reduction from baseline, but did have significance when thrombocytopenia was defined as platelet counts <143×10³/μL (data not shown). It is possible that the killed bacterin is needed to produce the reduction in the duration of thrombocytopenia, and is enhanced by the addition of the tandem repeat proteins. However, this dose of tandem repeat proteins as a stand-alone vaccine did not reduce the duration of thrombocytopenia.

There were significant differences in antibody titers in each vaccinated group (T02-T06) when compared to the control group (T01) on Days 28 (excluding T06), 49, 68, 69, and 70. All the vaccine preparations produced an antibody response to *E. canis* (data not shown). There was no significant difference between antibody titers for any vaccinated group (T02-T06) compared to T01 on Day 134 at the end of the study.

Treatment group comparisons of whether an animal had clinical disease or not post-challenge was not completed, as all animals had clinical disease, as defined by having at least one clinical sign post-challenge, with the exception of one animal in treatment group T03.

Clinically, the most relevant indication of disease caused by *E. canis* in a dog would be thrombocytopenia and fever. By this definition, 11 (91.7%) of the control animals had disease post-challenge; 8 (66.7%) of the animals in T02 and T03, the bacterin-only preparation groups, had disease post-challenge; 6 (50%) of the animals in T04, the bacterin and TRP co-administration group, had disease post-challenge; 9 (75%) of animals in the formalin bacterin preparation; and 10 (83.3%) of animals in T05, the TRP only vaccine group, had disease post-challenge.

The only significant improvement in disease post-challenge, as defined by fever+thrombocytopenia, compared to the control group (T01) was seen in the T04, whole cell, media-free bacterin vaccine+TRP vaccine, co-administered group (P=0.0399).

Conclusions

Efficacy in this study was determined based on the reduction of thrombocytopenia and clinical signs, namely fever, post-challenge. All animals were negative for *E. canis* by IDEXX SNAP 4Dx Plus and qPCR on Day 0.

Post-challenge, all control animals (T01) developed thrombocytopenia (primary variable). In contrast, only 7/12 animals in treatment group T04 had thrombocytopenia, a significant reduction (P=0.0141) compared to the T01 control group. The duration of thrombocytopenia (<143,000) in days was also shortened in the T04 co-administration vaccine group when compared to the T01 control group.

Post-challenge, 11/12 of the control animals (T01) developed fever (>39.7° C.). The animals in treatment group T04 developed fever post-challenge in 7/12 dogs. T02 and T03 developed fever post-challenge in 8/12 dogs, and T05 and T06 in 10/12 dogs post-challenge.

The co-administration vaccine group (T04) had a significant reduction is disease, when defined as thrombocytopenia and fever, post-challenge (P=0.0399). The vaccines co-administered to the T04 group (E. canis bacterin vaccine+ recombinant TRP protein vaccine) met the criteria for efficacy.

Example 2

Confirmation of Vaccine Efficacy of an *Ehrlichia canis* Bacterin and Recombinant TRP Antigens in Beagles The objective of this study is to confirm the preliminary efficacy of an *Ehrlichia* canis (*E. canis*) bacterin and recombinant Tandem Repeat Protein (TRP) vaccine, blended groups (12 animals/treatment group) using a randomized complete block design. Treatment groups are defined as T01—Saline controls, T02—[*E. canis* Sheba Whole Cell bacterin, BEI (binary ethyleneimine) inactivation+QCT] and [TRP 140, 36, 19+QCT] (co-administered), T03—*E. canis* Sheba Whole Cell bacterin, BEI inactivation+TRP 140, 36, 19+QCT (blended), T04—*E. canis* Whole Cell bacterin, BEI inactivation+QCT+Chimeric protein (Table 4).

All animals will be healthy and negative for *E. canis* on Day 0 by IDEXX SNAP 4DX and qPCR. All animals will be subcutaneously vaccinated with either placebo (saline) or Investigational Veterinary Product (IVP) on Days 0 and 28. Animals will be challenged via the intravenous route with *E. canis* Ebony strain three weeks after the second vaccination. Tympanic temperatures will be collected daily, and all animals will be observed daily for clinical signs of *E. canis* infection through the end of study. Blood samples will be collected for Complete Blood Chemistry (CBC) testing every three days post-challenge and will be tested by qPCR starting seven days post-challenge. Additional blood samples will be collected for IDEXX SNAP® 4Dx Plus and ELISA testing.

TABLE 4

| | | | Vaccination | | | | Blood | End of |
|---|---|---|---|---|---|---|---|---|
| TRT | # Animals | Treatment | Days[1] | Dose (ml) | Route | Challenge[2] | Collection | Study |
| T01 | 12 | Saline | 0, 28 | 1.0 | SQ | Day 49 | Days 0, 28, 35, 47-49, every 3rd day from 56-110 | Day 110 |
| T02 | 12 | [*E. canis* Sheba Whole Cell Bacterin (BEI inactivation) target 1.54E11 qPCR + QCT] and [TRP 140, 36, 19 + QCT] (co-administered) | | 1.0 of bacterin + 1.0 of TRP | | | | |
| T03 | 12 | *E. canis* Sheba Whole Cell Bacterin (BEI inactivation) target 1.54E11 qPCR + TRP 140, 36, 19 (blended vaccine) + QCT adjuvant | | 1.0 | | | | |
| T04 | 12 | *E. canis* Whole Cell Bacterin target 1.54E11 (BEI inactivation) + QCT adjuvant + Chimeric protein (@ 150 µg/mL) | | 1.0 | | | | |

STUDY DESIGN

[1]Vaccination on Day 0 will be performed over the right shoulder region. Vaccination on Day 28 will be performed over the left shoulder region.
[2]Target challenge dose will be 500 infected cells in 1.0 mL administered intravenously.

together and in an adjuvant formulation consisting of Quil A, cholesterol, and CpG (QCT), against a heterologous *E. canis* (Ebony strain) challenge in dogs approximately 12 weeks of age at first vaccination. Preliminary efficacy was previously established when separate vaccines containing the inactivated bacterin with QCT, and a vaccine containing the three TRP proteins and QCT, were co-administered subcutaneously 28 days apart. In addition, the efficacy of a vaccine containing both the bacterin and a chimeric *E. canis* protein will be evaluated.

Forty-eight (48) female beagles, approximately 12 weeks of age, will be randomly assigned to one of four treatment The primary variables will be thrombocytopenia (platelet count below $143 \times 10^3/\mu L$, or >50% reduction compared with pre-challenge levels) and clinical disease. A vaccine effect will be confirmed if the T02, T03, and/or T04 treatment groups have significantly less thrombocytopenia or clinical disease after challenge compared to T01 controls (p≤0.10). A vaccine effect will also be demonstrated if the lower bound of the 90% confidence interval of the matched-pair prevented fraction comparing T02, T03, and T04 to T01 is above 0. A vaccine effect will be confirmed if the duration of thrombocytopenia of at least one of the vaccinated groups is significantly shorter than in controls (T01), and/or if the lower bound of the 90% confidence interval is above 0 for the matched-pair mitigated fraction, as well as having a shift in the five number summary (minimum; $25^{th}$ percentile; median; $75^{th}$ percentile; and maximum).

Thrombocytopenia (treatment groups T01-T04) will be analyzed with a generalized linear mixed model, with a binomial distribution and a logit link function, if possible. The fixed effect will be treatment, and the random effect will be block. Otherwise, the data will be analyzed using Fisher's Exact test. The least squares means, standard errors, and 90% confidence intervals will be back-transformed if the generalized linear mixed model converges. Matched-pair prevented fractions of ever having thrombocytopenia will be calculated for treatment groups T02, T03, and T04 relative to T01, with their 90% confidence intervals. Pairing will be based on block.

Duration of thrombocytopenia based on platelet counts being $<143\times10^3/\mu L$, and $>50\%$ reduction from pre-challenge levels, will be calculated for each animal post-challenge. Duration will be the number of days from the first instance of thrombocytopenia through the last day, or 0 if the animal does not have thrombocytopenia. Duration will be analysed with general linear mixed model, with the fixed effect of treatment, and the random effects of block and residual. Treatment least squares means, standard errors, 90% confidence limits, minimums, and maximums will be calculated. Treatment group T01 will be compared to treatment groups T02, T03, and T04 using contrasts. Matched-pair mitigated fractions between T01 and the other treatment groups will be calculated, along with their 90% confidence limits. Pairing will be based on block.

Disease will be defined as an animal with fever (elevated body temperature $\geq39.5°$ C.) and thrombocytopenia (platelet counts being $<143\times10^3/\mu L$) at any time point post-challenge. Frequency distributions of clinical disease will be calculated for each treatment group. Clinical disease (treatment groups T01-T04) will be analyzed with a generalized linear mixed model, with a binomial distribution and a logit link function, if possible. The fixed effect will be treatment, and the random effect will be block. Otherwise, the data will be analyzed using Fisher's Exact test. Treatment groups T02-T04 will be compared to T01 using contrasts. The least squares means, standard errors, and 90% confidence intervals will be back-transformed if the generalized linear mixed model converges. Matched-pair prevented fractions of ever having clinical disease will be calculated for treatment groups T02, T03, and T04 relative to T01, with their 90% confidence intervals. Pairing will be based on block.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

European Patent 2433646
U.S. Pat. No. 4,373,932
U.S. Pat. No. 4,220,450
U.S. Pat. No. 4,897,268
U.S. Pat. No. 4,472,509
U.S. Pat. No. 4,938,948
U.S. Pat. No. 5,075,109
U.S. Pat. No. 5,440,013
U.S. Pat. No. 5,446,128
U.S. Pat. No. 5,470,723
U.S. Pat. No. 5,470,932
U.S. Pat. No. 5,543,504
U.S. Pat. No. 5,552,157
U.S. Pat. No. 5,565,213
U.S. Pat. No. 5,567,434
U.S. Pat. No. 5,618,914
U.S. Pat. No. 5,656,016
U.S. Pat. No. 5,670,155
U.S. Pat. No. 5,697,899
U.S. Pat. No. 5,738,868
U.S. Pat. No. 5,741,516
U.S. Pat. No. 5,770,219
U.S. Pat. No. 5,779,708
U.S. Pat. No. 5,783,208
U.S. Pat. No. 5,795,587
U.S. Pat. No. 5,797,898
U.S. Pat. No. 5,840,833
U.S. Pat. No. 5,853,744
U.S. Pat. No. 5,859,184
U.S. Pat. No. 5,891,506
U.S. Pat. No. 5,929,237
U.S. Pat. No. 6,136,610
U.S. Pat. No. 6,210,708
U.S. Pat. No. 6,372,445
U.S. Pat. No. 6,617,142
U.S. Pat. No. 6,875,750
U.S. Pat. No. 6,951,765
U.S. Pat. No. 7,163,677
U.S. Pat. No. 7,204,992
U.S. Pat. No. 7,282,194
U.S. Pat. No. 7,344,893
U.S. Pat. No. 7,371,582
U.S. Pat. No. 8,580,280
U.S. Pat. No. 8,980,288
U.S. Pat. No. 9,250,240
U.S. Pat. No. 9,545,439
U.S. Pat. No. 9,645,148
U.S. Pat. No. 9,662,385
U.S. Pat. No. 10,117,921
U.S. Pat. No. 10,238,736
U.S. Patent Appln. 2005/0047972
U.S. Patent Appln. 2005/0065463
U.S. Patent Appln. 2005/0250141
U.S. Patent Appln. 2007/0264664
U.S. Patent Appln. 2009/0005535
U.S. Patent Appln. 2019/0008953
U.S. Patent Appln. 2019/0038737
WO2005087803
Aguiar et al. Ticks Tick Borne Dis. 2016 February; 7(1): 142-145.
Aucouturier, et al. (2002) Montanide ISA 720 and 51: a new generation of water in oil emulsions as adjuvants for human vaccines. *Expert Rev. Vaccines* 1, 111-118.
Billeskov, et al. (2016) Testing the H56 vaccine delivered in 4 different adjuvants as a BCG-booster in a non-human primate model of tuberculosis. *PLoS One* 11, e0161217.

Bonam et al., Trends in Pharmacological Sciences (2017) 38(9): 771-778.

Calabro et al. (2013) *Vaccine* 31: 3363-3369

Carpino et al., *Org. Proc. Res. Dev.,* 7(1)28-37, 2003.

Didierlaurent, et al. (2009) AS04, an aluminum salt- and TLR4 agonist-based adjuvant system, induces a transient localized innate immune response leading to enhanced adaptive immunity *J. Immunol.* 183, 6186-6197.

Didierlaurent, et al. (2014) Enhancement of adaptive immunity by the human vaccine adjuvant AS01 depends on activated dendritic cells. *J. Immunol.* 193, 1920-1930.

Dumler et al., *Clin. Infect. Dis.,* 45:S45-S51, 2007.

Feng and Walker, *Infect. Immun.,* 72:966-971, 2004.

Fishbein et al., Human ehrlichiosis in the United States, 1985 to 1990. AnnInternMed 120:736-743, 1994.

Garcon and Van Mechelen (2011) Recent clinical experience with vaccines using MPL- and QS-21-containing adjuvant systems. *Expert Rev. Vaccines* 10, 471-486.

Geysen et al., *Proc. Natl. Acad. Sci. USA,* 81(13):3998-4002, 1984.

He et al., Vaxign: the first web-based vaccine design program for reverse vaccinology and applications for vaccine development. J Biomed Biotechnol 2010:297505, 2010.

Hotopp et al., Comparative genomics of emerging human ehrlichiosis agents. PLoS Genet 2:e21, 2006.

Künzi, et al. (2009) Immunogenicity and safety of low dose virosomal adjuvanted influenza vaccine administered intradermally compared to intramuscular full dose administration. *Vaccine* 27, 3561-3567.

Kuriakose et al., *Ehrlichia chaffeensis* transcriptome in mammalian and arthropod hosts reveals differential gene expression and post transcriptional regulation. PLoS One 6:e24136, 2011.

Kuriakose et al., Molecular basis of antibody mediated immunity against *Ehrlichia chaffeensis* involves species-specific linear epitopes in tandem repeat proteins. Microbes Infect 14:1054-1063, 2012.

Li and Winslow, Survival, replication, and antibody susceptibility of *Ehrlichia chaffeensis* outside of host cells. InfectImmun 71:4229-4237, 2003.

Li et al., Antibodies highly effective in SCID mice during infection by the intracellular bacterium *Ehrlichia chaffeensis* are of picomolar affinity and exhibit preferential epitope and isotype utilization. JImmunol 169:1419-1425, 2002.

Li et al., Outer membrane protein-specific monoclonal antibodies protect SCID mice from fatal infection by the obligate intracellular bacterial pathogen *Ehrlichia chaffeensis.* JImmunol 166:1855-1862, 2001.

Lin et al., Global proteomic analysis of two tick-borne emerging zoonotic agents: *Anaplasma phagocytophilum* and *Ehrlichia chaffeensis.* Front Microbiol 2:24, 2011.

Magnan et al., High-throughput prediction of protein antigenicity using protein microarray data. Bioinformatics 26:2936-2943, 2010.

McBride and Walker, Progress and obstacles in vaccine development for the ehrlichioses. Expert Rev Vaccines 9:1071-1082, 2010.

McBride et al., Infect Immun. 2011 August; 79(8):3178-87.

McBride et al. Gene. 2000 Aug. 22; 254(1-2):245-52.

Mizuno et al., Chemistry.23(58):14394-14409, Oct. 17 2017.

Morel, et al. (2011) Adjuvant System AS03 containing a-tocopherol modulates innate immune response and leads to improved adaptive immunity *Vaccine* 29, 2461-2473.

Nandi et al., CD4 T-cell epitopes associated with protective immunity induced following vaccination of mice with an ehrlichial variable outer membrane protein. InfectImmun 75:5453-5459. 2007.

Olano et al., Human monocytotropic ehrlichiosis, Missouri. EmergInfectDis 9:1579-1586, 2003.

Paparone et al., Ehrlichiosis with pancytopenia and ARDS. New Jersey Med 92:381-385, 1995.

Paterson et al., Anal Chem. 86(19):9481-8, Oct. 7; 2014.

Pierce Immunotechnology Catalog and Handbook, at A12-A13, 1991

Racine et al., IgM production by bone marrow plasmablasts contributes to long-term protection against intracellular bacterial infection. J Immunol 186:1011-1021, 2011.

Remington: The Science and Practice of Pharmacy, 21st Ed. Lippincott Williams and Wilkins, 2005.

Remington's Pharmaceutical Sciences, 18th Ed. Mack Printing Company, 1289-1329, 1990.

Sotomay et al., Animal model of fatal human monocytotropic ehrlichiosis. AmJPath 158:757-769, 2001.

Stuen et al. (Acta Vet Scand (2015):57:40).

Tandrup Schmidt, et al. (2016) Liposome-based adjuvants for subunit vaccines: formulation strategies for subunit antigens and immunostimulators. *Pharmaceutics* 8, 7.

The Science and Practice of Pharmacy, 21' Ed. Lippincott Williams and Wilkins, 2005

Tollersrud et al., "*Staphylococcus aureus* capsular polysaccharide type 5 conjugate and whole cell vaccines stimulate antibody responses in cattle." (2001) *Vaccine* 19:3896-3903

Vega et al. (Vaccine (2007) 25:519-525.

Walker and Dumler, Human monocytic and granulocytic ehrlichioses. Discovery and diagnosis of emerging tick-borne infections and the critical role of the pathologist. [Review] [50 refs]. Archives of Pathology & Laboratory Medicine 121:785-791, 1997.

Walker et al., *Ehrlichia chaffeensis*: a prevalent, life-threatening, emerging pathogen. Trans Am Clin Climatol Assoc 115:375-382; discussion 382-374, 2004.

Winslow et al., *Ann. NY Acad. Sci.,* 990:435-443, 2003.

Winslow et al., *Infect. Immun.,* 68:2187-2195, 2000.

Winslow et al., Infection of the laboratory mouse with the intracellular pathogen *Ehrlichia chaffeensis.* InfectImmun 66:3892-3899, 1998.

Yager et al., *Infect. Immun.,* 73:8009-8016, 2005.

Zemella et al., Cell-Free Protein Synthesis: Pros and Cons of Prokaryotic and Eukaryotic Systems. *Chembiochem.;* 16(17):2420-2431, 2015.

Zhu et al., Infect Immun. 2011 November; 79(11):4370-81

What is claimed is:

1. An immunogenic composition comprising a suspension of an *Ehrlichia canis* bacterin and a combination of immunogenic tandem repeat proteins (TRP) consisting of isolated TRP36, TRP140 and TRP19 proteins of *Ehrlichia canis*, a pharmaceutically acceptable excipient, and an adjuvant formulation consisting of a purified or partially purified immunologically active saponin prepared from the bark of *Quillaja saponaria*, cholesterol, and a CpG-containing ODN, wherein the *Ehrlichia canis* bacterin is inactivated with binary ethyleneimine (BEI).

2. The immunogenic composition of claim 1, wherein the TRP19 protein comprises SEQ ID NO: 1, the TRP140 protein comprises SEQ ID NO: 14 and the TRP36 protein comprises one of SEQ ID NOs: 3 to 11.

3. The immunogenic composition of claim 1, wherein the TRP36 protein, the TRP140 protein and the TRP19 protein are produced recombinantly.

4. The immunogenic composition of claim 1, wherein the CpG-containing ODN is of SEQ ID NO: 17.

5. The immunogenic composition of claim 1, wherein the adjuvant formulation is an oil-in-water emulsion.

6. A method of inducing an immune response in a mammalian subject comprising administering to the subject a pharmaceutically relevant amount of the immunogenic composition of claim 1.

7. The method of claim 6, wherein the mammalian subject is a dog.

* * * * *

SEQUENCE LISTING

<160> NUMBER OF SEQ ID NOS: 17

<210> SEQ ID NO 1
<211> LENGTH: 24
<212> TYPE: PRT

-continued

```
<213> ORGANISM: Ehrlichia canis

<400> SEQUENCE: 1

His Phe Thr Gly Pro Thr Ser Phe Glu Val Asn Leu Ser Glu Glu Glu
1               5                   10                  15

Lys Met Glu Leu Gln Glu Val Ser
            20

<210> SEQ ID NO 2
<211> LENGTH: 21
<212> TYPE: PRT
<213> ORGANISM: Ehrlichia canis

<400> SEQUENCE: 2

Ala Lys Glu Glu Lys Asn Ala Thr Ala Lys Thr Phe Gln Leu Lys Gly
1               5                   10                  15

Asp Trp Asp Gly Ala
            20

<210> SEQ ID NO 3
<211> LENGTH: 9
<212> TYPE: PRT
<213> ORGANISM: Ehrlichia canis

<400> SEQUENCE: 3

Thr Glu Asp Ser Val Ser Ala Pro Ala
1               5

<210> SEQ ID NO 4
<211> LENGTH: 8
<212> TYPE: PRT
<213> ORGANISM: Ehrlichia canis

<400> SEQUENCE: 4

Ala Ser Val Val Pro Glu Ala Glu
1               5

<210> SEQ ID NO 5
<211> LENGTH: 9
<212> TYPE: PRT
<213> ORGANISM: Ehrlichia canis

<400> SEQUENCE: 5

Thr Glu Asp Pro Val Ser Ala Thr Ala
1               5

<210> SEQ ID NO 6
<211> LENGTH: 26
<212> TYPE: PRT
<213> ORGANISM: Ehrlichia spp.

<400> SEQUENCE: 6

Thr Glu Asp Ser Val Ser Ala Pro Ala Ala Ser Val Val Pro Glu Ala
1               5                   10                  15

Glu Thr Glu Asp Pro Val Ser Ala Thr Ala
            20                  25

<210> SEQ ID NO 7
<211> LENGTH: 26
<212> TYPE: PRT
<213> ORGANISM: Ehrlichia spp.

<400> SEQUENCE: 7
```

```
Thr Glu Asp Ser Val Ser Ala Pro Ala Thr Glu Asp Pro Val Ser Ala
1               5                   10                  15

Thr Ala Ala Ser Val Val Pro Glu Ala Glu
            20                  25

<210> SEQ ID NO 8
<211> LENGTH: 26
<212> TYPE: PRT
<213> ORGANISM: Ehrlichia spp.

<400> SEQUENCE: 8

Ala Ser Val Val Pro Glu Ala Glu Thr Glu Asp Ser Val Ser Ala Pro
1               5                   10                  15

Ala Thr Glu Asp Pro Val Ser Ala Thr Ala
            20                  25

<210> SEQ ID NO 9
<211> LENGTH: 26
<212> TYPE: PRT
<213> ORGANISM: Ehrlichia spp.

<400> SEQUENCE: 9

Ala Ser Val Val Pro Glu Ala Glu Thr Glu Asp Pro Val Ser Ala Thr
1               5                   10                  15

Ala Thr Glu Asp Ser Val Ser Ala Pro Ala
            20                  25

<210> SEQ ID NO 10
<211> LENGTH: 26
<212> TYPE: PRT
<213> ORGANISM: Ehrlichia spp.

<400> SEQUENCE: 10

Thr Glu Asp Pro Val Ser Ala Thr Ala Thr Glu Asp Ser Val Ser Ala
1               5                   10                  15

Pro Ala Ala Ser Val Val Pro Glu Ala Glu
            20                  25

<210> SEQ ID NO 11
<211> LENGTH: 26
<212> TYPE: PRT
<213> ORGANISM: Ehrlichia spp.

<400> SEQUENCE: 11

Thr Glu Asp Pro Val Ser Ala Thr Ala Ala Ser Val Val Pro Glu Ala
1               5                   10                  15

Glu Thr Glu Asp Ser Val Ser Ala Pro Ala
            20                  25

<210> SEQ ID NO 12
<211> LENGTH: 24
<212> TYPE: PRT
<213> ORGANISM: Ehrlichia canis

<400> SEQUENCE: 12

Asp Asp Ser Lys Leu Pro Val Ile Lys Val Glu Asp Lys Ser Lys Leu
1               5                   10                  15

Gln Asp Thr Lys Asp Lys Lys Arg
            20

<210> SEQ ID NO 13
<211> LENGTH: 19
```

```
<212> TYPE: PRT
<213> ORGANISM: Ehrlichia canis

<400> SEQUENCE: 13

Lys Lys Ile Lys Glu Tyr Asp Glu Asp Tyr Thr Ile Thr Tyr Tyr Tyr
1               5                   10                  15

Asp Asp Asp

<210> SEQ ID NO 14
<211> LENGTH: 25
<212> TYPE: PRT
<213> ORGANISM: Ehrlichia canis

<400> SEQUENCE: 14

Glu His Ser Ser Ser Glu Val Gly Glu Lys Val Ser Glu Thr Ser Lys
1               5                   10                  15

Glu Glu Asn Thr Pro Glu Val Lys Ala
            20                  25

<210> SEQ ID NO 15
<211> LENGTH: 22
<212> TYPE: PRT
<213> ORGANISM: Ehrlichia chaffeensis

<400> SEQUENCE: 15

Ser Lys Val Glu Gln Glu Glu Thr Asn Pro Glu Val Leu Ile Lys Asp
1               5                   10                  15

Leu Gln Asp Val Ala Ser
            20

<210> SEQ ID NO 16
<211> LENGTH: 28
<212> TYPE: PRT
<213> ORGANISM: Ehrlichia canis

<400> SEQUENCE: 16

Glu Ala Ser Val Val Pro Ala Ala Glu Ala Pro Gln Pro Ala Gln Gln
1               5                   10                  15

Thr Glu Asp Glu Phe Phe Ser Asp Gly Ile Glu Ala
            20                  25

<210> SEQ ID NO 17
<211> LENGTH: 24
<212> TYPE: DNA
<213> ORGANISM: Artificial sequence
<220> FEATURE:
<223> OTHER INFORMATION: Synthetic oligo
<220> FEATURE:
<221> NAME/KEY: misc_feature
<222> LOCATION: (1)..(1)
<223> OTHER INFORMATION: n = 5'-Iodo-2'-deoxyuridine
<220> FEATURE:
<221> NAME/KEY: misc_binding
<222> LOCATION: (1)..(24)
<223> OTHER INFORMATION: phosphodiester bond

<400> SEQUENCE: 17
ncgtcgacga tcggcggccg ccgt                                                    24
```